United States Patent
Yoo (10) Patent No.: US 10,309,942 B2
(45) Date of Patent: Jun. 4, 2019

(54) PORTABLE DEVICE AND METHOD FOR MEASURING GAS IN CLOSED SPACE

(71) Applicant: ELECTRONICS AND TELECOMMUNICATIONS RESEARCH INSTITUTE, Daejeon (KR)

(72) Inventor: Dae Seung Yoo, Ulsan (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 78 days.

(21) Appl. No.: 15/450,552

(22) Filed: Mar. 6, 2017

(65) Prior Publication Data

US 2017/0370891 A1 Dec. 28, 2017

(30) Foreign Application Priority Data

Jun. 22, 2016 (KR) .................. 10-2016-0077855

(51) Int. Cl.
*G01N 33/00* (2006.01)

(52) U.S. Cl.
CPC ....... *G01N 33/0031* (2013.01); *G01N 33/004* (2013.01); *G01N 33/0011* (2013.01); *G01N 33/0044* (2013.01); *G01N 33/0047* (2013.01); *G01N 33/0075* (2013.01)

(58) Field of Classification Search
CPC .......... G01N 33/0031; G01N 33/0011; G01N 33/004; G01N 33/0044; G01N 33/0047; G01N 33/0075; G01N 33/0073

USPC ....... 73/23.2–31.07, 335.01–335.14; 702/24, 702/127; 340/603, 627–634, 870.02, 340/870.03, 870.16

See application file for complete search history.

(56) References Cited

U.S. PATENT DOCUMENTS

| | | | |
|---|---|---|---|
| 7,738,104 B2 | 6/2010 | Kim et al. | |
| 2002/0144537 A1* | 10/2002 | Sharp | G01N 1/26 73/31.01 |
| 2009/0153864 A1 | 6/2009 | Kim et al. | |
| 2012/0319863 A1* | 12/2012 | Sato | G01N 27/622 340/870.02 |

(Continued)

FOREIGN PATENT DOCUMENTS

| | | |
|---|---|---|
| KR | 20-0390989 Y1 | 7/2005 |
| KR | 10-1202614 B1 | 11/2012 |
| KR | 10-2015-0022143 A | 3/2015 |

*Primary Examiner* — Robert R Raevis
(74) *Attorney, Agent, or Firm* — LRK Patent Law Firm (57) ABSTRACT

A portable device for measuring gas in a closed space includes an air intake and exhaust unit configured to suction external air and discharge the suctioned air, a sensor unit configured to measure characteristics of the air suctioned by the air intake and exhaust unit, a communication unit configured to communicate with a host system, a power supply unit configured to supply power to the air intake and exhaust unit, the sensor unit, and the communication unit, and a control unit configured to control the air intake and exhaust unit, the sensor unit, the communication unit, and the power supply unit so that the sensor unit measures the characteristics of the air suctioned by the air intake and exhaust unit and configured to transmit measurement information to the host system through the communication unit.

25 Claims, 5 Drawing Sheets

(56) References Cited

U.S. PATENT DOCUMENTS

2015/0004898 A1* 1/2015 Desrochers ........ G01N 33/0054
                                                    454/239
2015/0021716 A1  1/2015 Lee et al.
2015/0250408 A1* 9/2015 Ssenyange ............. A61B 5/097
                                                    600/532
2016/0223552 A1* 8/2016 Kizuka ............ G01N 33/57419

* cited by examiner

PORTABLE DEVICE AND METHOD FOR MEASURING GAS IN CLOSED SPACE

CROSS-REFERENCE TO RELATED APPLICATION

This application claims priority to and the benefit of Korean Patent Application No. 10-2016-0077855, filed on Jun. 22, 2016, the disclosure of which is incorporated herein by reference in its entirety.

BACKGROUND

1. Field

The present invention relates to a technology for measuring gas in a closed space, and more particularly, to a portable device and method for measuring gas in a closed space so that a safe work environment may be provided to a worker in a closed space and power consumption thereof may be reduced.

2. Description of Related Art

Recently, along with an increase in social concerns about disaster safety management and a response system at an industrial site due to major accidents that result in injury or death, there is an increasing need for a control and response system that utilizes Internet of Things (IoT) convergence technology.

While it is difficult to establish an advanced IoT-based disaster safety management system at an industrial site because of the aftermath of a recession, establishing an advanced IoT-based disaster safety management system at a very dangerous industrial site, which has a high probability that an accident, such as a fire or an explosion, will take place and huge human and material damages can be expected when such an accident takes place, can no longer be postponed.

It is very dangerous to perform an operation, such as a manufacturing process, in a closed space that is perfectly shielded from the outside, and an accident resulting in injury or death of a worker often occurs in association with an accident such as a harmful gas leak or a fire in a closed space.

In particular, it is difficult to identify a change to an environment that may be a harmful factor in a metal compartment, which is a space where communication with the outside is perfectly blocked, in real time, and it is not easy to take an initial action even when a serious accident happens to a worker.

Also, a supervisor should measure concentrations of oxygen and a harmful gas before a worker enter a closed space in accordance with an increase in the risk of suffocation, a fire, and an explosion of the worker in the closed space.

A method of measuring oxygen and a harmful gas in a closed space includes a measurement method that uses a personal portable measurement device and a measurement method that is performed by inserting a suction hose into a closed space and suctioning gas in the closed space with a gas suction pump.

When gas is measured using a portable measurement device, the portable measurement device has technical problems in that the device should be small and light to provide portability while also being capable of precise measurement and also in that the device should be designed to consume little power because a battery should be used as a power source thereof.

Also, the method that uses a pump has a problem in that it is difficult to move and install a suction hose and pump before entering a closed space.

SUMMARY

The present invention provides a portable device and method for measuring gas in a closed space to which next-generation IoT wireless communication is applied. The gas measuring device is capable of precisely measuring concentrations of oxygen and a harmful gas and is designed to have low power consumption enabling a long use time.

According to an aspect of the present invention, there is provided a portable device for measuring gas in a closed space, the gas measuring device including an air intake and exhaust unit configured to suction external air and discharge the suctioned air; a sensor unit configured to measure characteristics of the air suctioned by the air intake and exhaust unit; a communication unit configured to communicate with a host system; a power supply unit configured to supply power to the air intake and exhaust unit, the sensor unit, and the communication unit; and a control unit configured to control the air intake and exhaust unit, the sensor unit, the communication unit, and the power supply unit so that the sensor unit measures the characteristics of the air suctioned by the air intake and exhaust unit and configured to transmit measurement information to the host system through the communication unit.

The sensor unit may include an oxygen ($O_2$) sensor, a carbon monoxide (CO) sensor, a hydrogen sulfide ($H_2S$) sensor, a hydrogen ($H_2$) sensor, and a methane ($CH_4$) sensor.

The control unit may control the power supply unit to supply power to the oxygen sensor, the carbon monoxide sensor, the hydrogen sulfide sensor, and the hydrogen sensor and may control the power supply unit to supply power to the methane sensor when a concentration of hydrogen measured by the hydrogen sensor exceeds a reference value.

The control unit may be configured to control the air intake and exhaust unit, the sensor unit, the communication unit, and the power supply unit after the control unit is activated from a sleep state according to an event signal.

The control unit may be activated by using an interrupt generated by a timer included in the control unit as the event signal.

The gas measuring device may further include an operation unit configured to generate a plurality of electric signals according to an operation of a user in order to control the gas measuring device. The control unit may be activated by using an operation start signal generated by the operation unit as the event signal.

The control unit may be activated by using a wake-up signal transmitted from the host system as the event signal.

The air intake and exhaust unit may include: a body; an intake port formed at one side of the body and configured to suction external air; an exhaust port formed at another side of the body and configured to discharge the air suctioned through the intake port; an air pump configured to enable air to be suctioned through the intake port and discharged through the exhaust port; and a pipe configured to connect the intake port to the exhaust port. The pipe may include spaces with a certain size in which the air stays for a predetermined time and a connector configured to connect the spaces.

The oxygen sensor, the carbon monoxide sensor, the hydrogen sulfide sensor, the hydrogen sensor, and the methane sensor may be arranged to correspond to the spaces and configured to measure gas to be measured that is included in air passing through the spaces.

The control unit may control the power supply unit to supply power to the sensor unit, supply power to the air intake and exhaust unit after a stabilization time, and stop the supply of power to the sensor unit and the air intake and exhaust unit when the measurement of the sensor unit is complete, and then supply power to the communication unit.

The gas measuring device may further include a warning unit configured to warn about a danger according to control of the control unit; an external power connector connected to the power supply unit and configured to supply external power to the power supply unit; and a display unit configured to display a state of the gas measuring device according to control of the control unit.

The display unit may include a first display composed of a plurality of light emitting diodes (LEDs) and configured to use light to display the state of the gas measuring device; and a second display configured to use figures or characters to display the state of the gas measuring device.

The second display may display a screen for setting a threshold of information measured by the sensor unit and an interval at which the measurement information is transmitted, and may provide information input through the screen to the control unit.

According to another aspect of the present invention, there is provided a method of measuring gas in a closed space using a portable gas measuring device, the method including activating the portable gas measuring device according to an event signal; supplying power to an oxygen ($O_2$) sensor, a carbon monoxide (CO) sensor, a hydrogen sulfide ($H_2S$) sensor, a hydrogen ($H_2$) sensor, and an air pump to measure a concentration of gas to be measured that is included in air suctioned by the air pump; determining whether a concentration of hydrogen gas measured by the hydrogen sensor exceeds a reference value; stopping the supply of power to the oxygen sensor, the carbon monoxide sensor, the hydrogen sulfide sensor, the hydrogen sensor, and the air pump when the concentration of the hydrogen gas does not exceed the reference value; and supplying power to a communication unit and transmitting measurement information to a host system through the communication unit.

The method may further include supplying power to a methane ($CH_4$) sensor to measure a concentration of methane gas included in the air and, stopping the supply of power to the oxygen sensor, the carbon monoxide sensor, the hydrogen sulfide sensor, the hydrogen sensor, the methane sensor, and the air pump when the concentration of the hydrogen gas exceeds the reference value.

The supplying of power to the oxygen sensor, the carbon monoxide sensor, the hydrogen sulfide sensor, the hydrogen sensor, and the air pump may include supplying power to the air pump when a stabilization time passes after power is supplied to the oxygen sensor, the carbon monoxide sensor, the hydrogen sulfide sensor, and the hydrogen sensor.

The event signal may be an interrupt generated by a built-in timer, an operation start signal generated by an operation of a user, or a wake-up signal input from the outside.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Advantages and features of the present invention and implementation methods thereof will be clarified through following embodiments described with reference to the accompanying drawings. The present invention may, however, be embodied in different forms and is not to be construed as limited to the embodiments set forth herein. Rather, these embodiments are provided so that this disclosure will be thorough and complete and will fully convey the scope of the present invention to those skilled in the art. The terminology used herein is for the purpose of describing particular embodiments only and is not intended to be limiting of example embodiments. As used herein, the singular forms "a," "an," and "the" are intended to include the plural forms as well unless clearly indicated otherwise by context. It should be further understood that the terms "comprises" or "comprising" specify the presence of stated features, integers, steps, operations, elements, and/or components when used in this specification, but do not preclude the presence or addition of one or more other features, integers, steps, operations, elements, components, and/or groups thereof.

Hereinafter, a portable device and method for measuring gas in a closed space according to an example embodiment of the present invention will be described in detail below with reference to the accompanying drawings.

Before the present invention is described in detail, a closed-space safety management system to which the present invention is applied will be briefly described with reference to FIG. 1.

Figure 1:
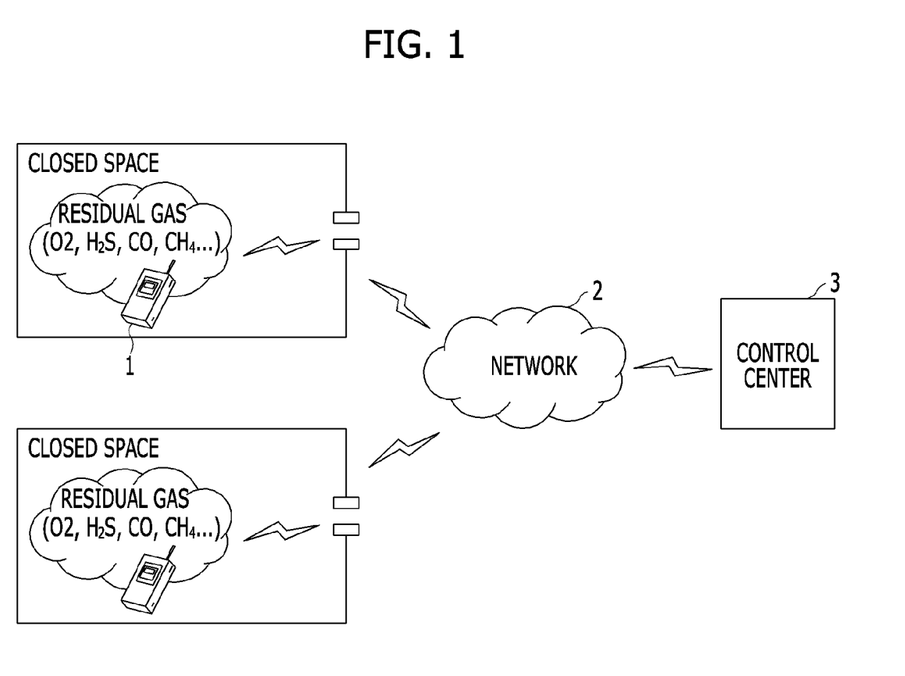
FIG. 1 is a diagram showing a network connection configuration of a closed-space safety management system to which the present invention is applied.

FIG. 1 is a diagram showing a network connection configuration of a closed-space safety management system to which the present invention is applied.

As shown in FIG. 1, an IoT-based portable gas measuring device 1 (hereinafter referred to as a gas measuring device) according to an embodiment of the present invention collects environmental information from a temperature and humidity sensor and gas sensors for $O_2$, CO, $H_2$, $H_2S$, $CH_4$, etc., in a closed work place and transmits the collected information to a remote control center 3, which is a host system, over a network 2.

Also, the gas measuring device 1 receives control and management information from the control center 3 and generates an event and an alarm when a management reference is exceeded.

The control center 3 performs safety management on a worker on the basis of a dangerous region information DB and information collected from a work place and transmits a warning of danger such as an evacuation alarm to the gas measuring device 1 over the network 2 when there is danger.

Also, when the detected data exceeds a management reference value, the control center 3 may control the gas measuring device 1 to generate an event and an alarm for danger.

The portable gas measuring device according to an embodiment of the present invention will be described in detail below with reference to FIG. 2.

Figure 2:
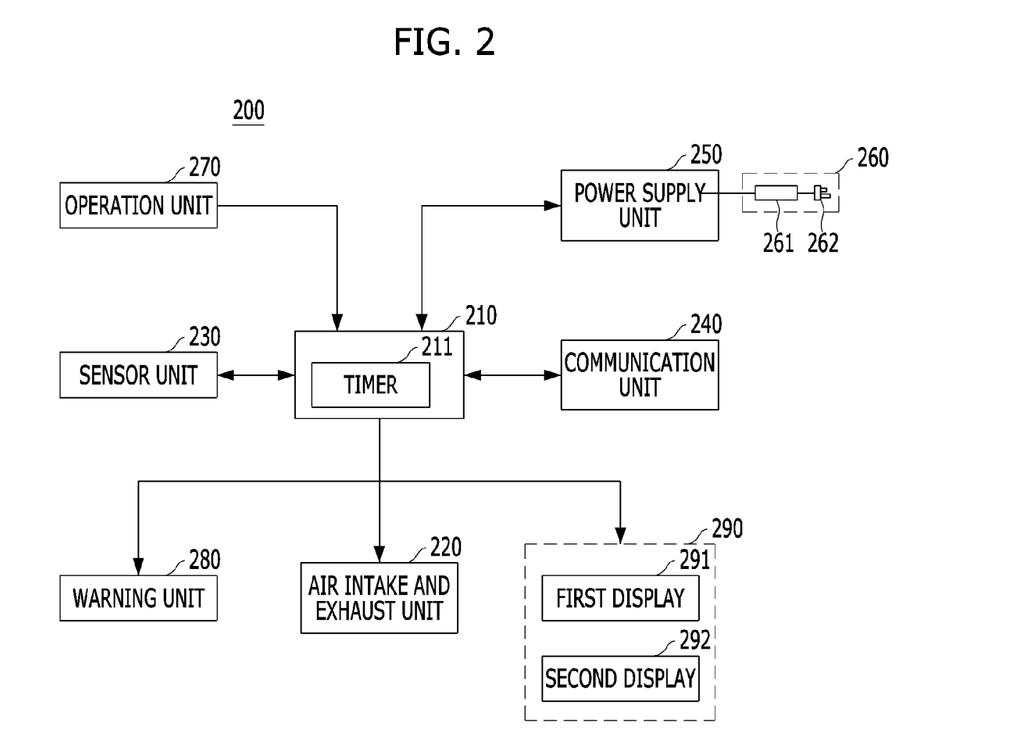
FIG. 2 is a diagram showing a configuration of a portable gas measurement device according to an embodiment of the present invention.

FIG. 2 is a diagram showing a configuration of a portable gas measurement device according to an embodiment of the present invention.

First, as shown in FIG. 2, a portable gas measuring device 200 (hereinafter referred to as a gas measuring device) according to an embodiment of the present invention is applied to the gas measuring device 1 of FIG. 1 and configured to detect a predetermined gas. The gas measuring device 200 may include a control unit 210, an air intake and exhaust unit 220, a sensor unit 230, a communication unit 240, and a power supply unit 250.

Additionally, the gas measuring device 200 may further include at least one of an external power connection unit 260, an operation unit 270, a warning unit 280, and a display unit 290. In this case, the gas measuring device 200 may be used in a closed space and may be configured to transmit measurement information to the outside, for example, to the control center 3 of FIG. 1, through IoT-based wireless communication.

However, a configuration of the gas measuring device 200 shown in FIG. 2 is merely an example for describing the present invention. The gas measuring device 200 is not limited to the elements shown in FIG. 2, and may include other elements.

The control unit 210 may be configured to control overall operation of the gas measuring device 1 and operate on the basis of power supplied from the power supply unit 250.

Also, the control unit 210 controls the air intake and exhaust unit 220 so that air may pass through the sensor unit 230, collects information detected by the sensor unit 230 (that is, the measurement information), and transmits the collected measurement information to, for example, the control center 3 of FIG. 1 through the communication unit 240.

Also, the control unit 210 may control the power supply unit 250 so that the power supply unit 250 supplies power to the air intake and exhaust unit 220, the sensor unit 230, and the communication unit 240 or cuts off the power supplied to the air intake and exhaust unit 220, the sensor unit 230, and the communication unit 240.

Also, the control unit 210 analyzes the measured information collected from the sensor unit 230 and controls the warning unit 280 to warn about danger when the collected measured information exceeds a threshold.

Alternatively, the control unit 210 may control the warning unit 280 to warn about danger according to a command from a host system, for example, the control center 3 of FIG. 1.

Also, the control unit 210 may identify a state of the communication unit 240, a state of the power supply unit 250, and a state of the warning unit 280 and provide the identified states to the display unit 290.

In this case, the control unit 210 may be activated in a sleep state according to a predetermined event signal and then perform a predetermined operation. The control unit 210 may be deactivated when the operation is complete.

As an example of the activation of the control unit 210, the control unit 210 includes a timer 211 that generates an interrupt at predetermined time intervals. The control unit 210 may be activated by using the interrupt generated by the timer 211 as the event signal. In this case, the interval at which the interrupt is generated may be set by a host system, for example, the control center 3 of FIG. 1, or directly by a user.

As another example of the activation of the control unit 210, the gas measuring device 200 includes the operation unit 270 that generates an electric signal according to a user's operation, and the control unit 210 may be activated by using the electric signal generated by the operation unit 270 as the event signal.

Thus, the gas measuring device 200 according to an embodiment of the present invention may include at least one of the timer 211 and the operation unit 270 in order to activate the control unit 210. However, the control unit 210 may be activated by other methods.

As still another example of the activation of the control unit 210, when an external device transmits a wake-up signal to the gas measuring device 200 to perform communication according to an information request, the wake-up signal may be input to the control unit 210, and control unit 210 may be activated by using the wake-up signal as the event signal.

When the control unit 210 is activated to perform an operation, the control unit 210 may drive a second display 292.

The air intake and exhaust unit 220 operates according to control of the control unit 210 and also operates based on power supplied from the power supply unit 250. The air intake and exhaust unit 220 is configured to suction air from the outside and discharge the suctioned air to the outside.

The air that is suctioned through the air intake and exhaust unit 220 passes through the sensor unit 230 and then is discharged through the air intake and exhaust unit 220.

Accordingly, the air intake and exhaust unit 220 should be designed in consideration of a relationship thereof with the sensor unit 230. This will be described below with reference to FIG. 3.

The sensor unit 230 measures characteristics of the air suctioned by the air intake and exhaust unit 220. Depending on a purpose thereof, the sensor unit 230 may be composed of a plurality of sub-sensor units. The sensor unit 230 will be described below with reference to FIG. 4.

The communication unit 240 may operate based on power provided from the power supply unit 250. The communication unit 240 receives measurement information provided from the control unit 210 and transmits the measurement information to the outside, for example, to the control center 3 of FIG. 1. The communication unit 240 receives control information transmitted from the control center 3 and provides the control information to the control unit 210.

Since a low power consumption design is a requirement for a portable gas measuring device, it is preferable that the communication unit 240 be designed to have little power consumption and enable long distance communication while being suitable for a special environment such as a closed space.

Thus, it is preferable that the communication unit 240 should include, for example, a LoRa communication module, a Zigbee communication module, or a Bluetooth low energy (BLE) communication module and perform communication in a LoRa WAN communication method, a Zigbee communication method, or a BLE communication method.

The power supply unit 250 supplies power to elements of the gas measuring device 200, for example, the control unit 210, the air intake and exhaust unit 220, the sensor unit 230, and the communication unit 240. In particular, the power supply unit 250 supplies power to the air intake and exhaust unit 220, the sensor unit 230, and the communication unit 240 or stops the supply of power according to control of the control unit 210.

The power supply unit 250 may be implemented as a rechargeable secondary battery. There is no limitation on the type and form of the secondary battery. The power supply unit 250 may be connected to and charged by the external power connection unit 260.

The external power connection unit 260 is connected to the power supply unit 250 and supplies external power to the power supply unit 250. The external power connection unit 260 may be fixed to or detachable from the power supply unit 250.

For example, the external power connection unit 260 may include an external power connector 261 connected to an external power source and an adapter 262 configured to convert external power supplied through the external power connector 261 into power suitable for the power supply unit 250 and provide the power to the power supply unit 250.

The operation unit 270 is included so that a user may control the gas measuring device 200. The user may operate the operation unit 270 to operate the gas measuring device 200 or stop the operation of the gas measuring device 200.

To this end, the operation unit 270 includes a plurality of switches that generate different electric signals. An electric signal generated by the operation unit 270 is transmitted to the control unit 210.

For example, the operation unit 270 may include a start button for generating an electric signal for starting operation of the gas measuring device 200 (i.e., an operation start signal) and a stop button for generating an electric signal for stopping the operation of the gas measuring device 200 (i.e., an operation stop signal), and may also include a button for another purpose.

In particular, the operation stop signal generated by the operation unit 270 is used as an event signal for activating the control unit 210.

The warning unit 280 is configured to warn about danger according to control of the control unit 210, and may generate a warning sound.

The display unit 290 may include a first display 291 and the second display 292 in order to display a state of the gas measuring device 200.

The first display 291 may be configured to display the state of the gas measuring device 200 using light. The first display 291 may include a light-emitting diode (LED) that shows a power state, an LED that shows a communication state, an LED that shows a warning level, etc. of the gas measuring device 200, and may also include an LED for another purpose.

In this case, the first display 291 may display a power state, a communication state, and a warning level of the gas measuring device 200 on the basis of information provided from the power supply unit 250, the communication unit 240, and the warning unit 280.

Alternatively, the first display 291 may display a power state, a communication state, and a warning level of the gas measuring device 200 on the basis of information provided from the control unit 210.

The second display 292 may be configured to display a state of the gas measuring device 200 using figures or characters and also display a screen for receiving a command from the outside.

In this case, the second display 292 may be driven by control of the control unit 210 when the control unit 210 receives the operation start signal generated by the operation unit 270. That is, the control unit 210 is driven when the control unit 210 receives the operation start signal from the operation unit 270, and then the control unit 210 controls the second display 292 to be driven.

In particular, the second display 292 displays a screen for setting a threshold of information measured by a sensor, an interval at which measurement information is transmitted, etc., and provides information input through the screen to the control unit 210.

The intake and exhaust unit 220 and the sensor unit 230 according to an embodiment of the present invention will be described in detail below with reference to FIGS. 3 and 4.

Figure 3:
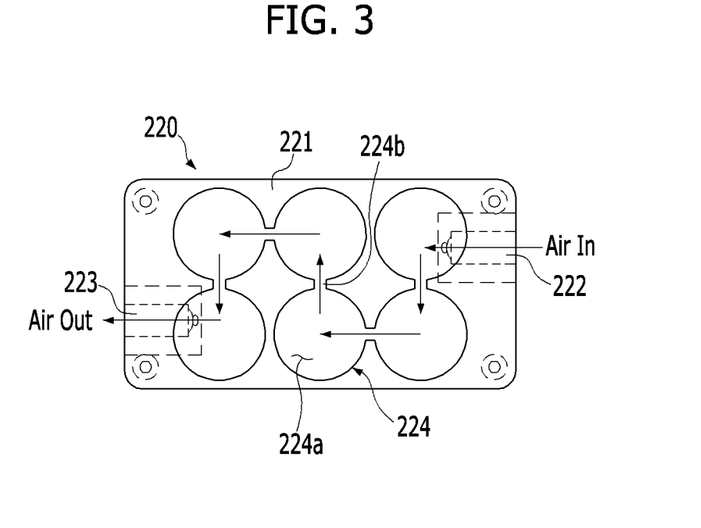
FIG. 3 is an example diagram showing a structure of an air intake and exhaust unit according to an embodiment of the present invention.

FIG. 3 is an example diagram showing a structure of an intake and exhaust unit according to an embodiment of the present invention.

Referring to FIG. 3, the intake and exhaust unit 220 according to an embodiment of the present invention includes a body 221, an intake port 222, an exhaust port 223, and a pipe 224. Though not shown in FIG. 3, the intake and exhaust unit 220 includes an air pump for suctioning air through the intake port 222 and discharging air through the exhaust port 223.

The intake port 222 is an element formed at one side of the body 221 and configured to suction air, and the exhaust port 223 is an element formed at the other side of the body 221 and configured to discharge the air suctioned through the intake port 222.

Also, the pipe 224 connects the intake port 222 to the exhaust port 223. Air suctioned through the intake port 222 moves along the pipe 224 and is discharged through the exhaust port 223. That is, the pipe 224 serves to guide the air suctioned through the intake port 222 to the exhaust port 223.

In this case, since the air that is moving along the pipe 224 should be measured by the sensor unit 230, the pipe 224 should be formed in an appropriate shape depending on a shape and position of the sensor unit 230.

In this embodiment, spaces 224a with a certain size in which air to be measured by the sensor unit 230 may stay for a predetermined time are provided in the pipe 224, and sensors of the sensor unit 230 are provided to correspond to the spaces 224a and configured to detect the air.

Also, a connector 224b for connecting the spaces 224a is provided in the pipe 224, and the pipe 224 includes the spaces 224a and the connector 224b.

Figure 4:
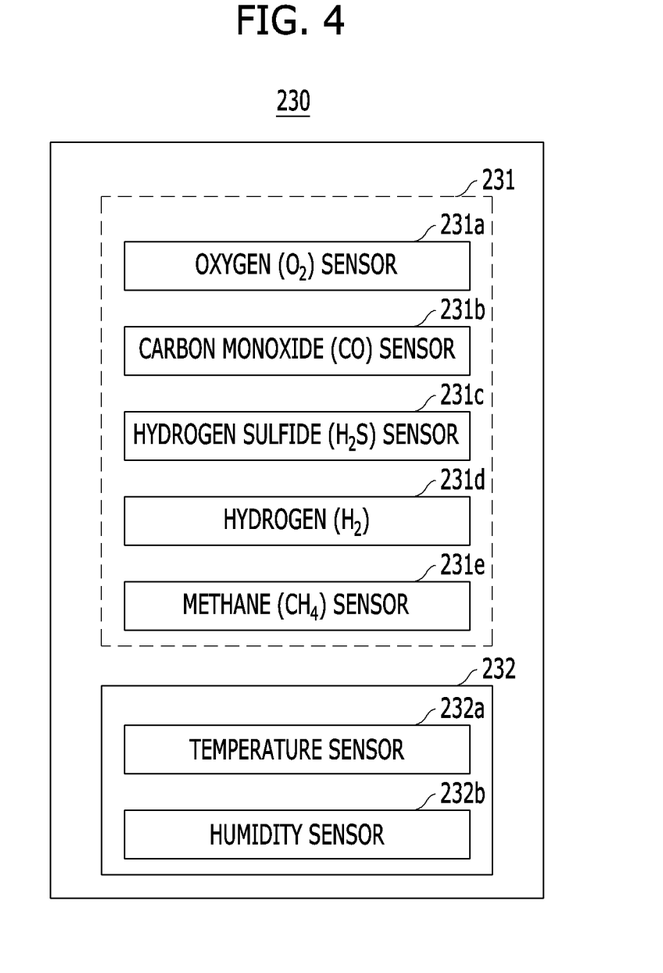
FIG. 4 is an example diagram showing a configuration of a sensor unit according to an embodiment of the present invention.

FIG. 4 is an example diagram showing a configuration of a sensor unit according to an embodiment of the present invention. Referring to FIG. 4, the sensor unit 230 may include a gas sensor unit 231 for measuring gas and a temperature and humidity sensor unit 232 for measuring temperature and humidity as sub-sensor units.

Each of the sub-sensor units 231 and 232 constituting the sensor unit 230 includes at least one or more sensors. In particular, the gas sensor unit 231 includes an oxygen ($O_2$) sensor 231a, a carbon monoxide (CO) sensor 231b, a hydrogen sulfide ($H_2S$) sensor 231c, a hydrogen ($H_2$) sensor 231d, and a methane ($CH_4$) sensor 231e. The sensors 231a to 231e are publicly known, and detailed descriptions of the sensors 231a to 231e will be omitted.

The methane ($CH_4$) sensor should be used to detect an explosive lower limit of a combustible gas (a hydrocarbon series), but has a power consumption that is 20 times greater than those of other sensors. For a low power consumption design, this embodiment proposes a method of reducing energy consumption by using a characteristic in which the hydrogen ($H_2$) sensor reacts very weakly to a combustible gas when the hydrogen ($H_2$) sensor is exposed to the combustible gas.

Also, in this embodiment, the sensor unit 230 may include the temperature and humidity sensor unit 232 that is formed as one module to measure both temperature and humidity. In this case, the temperature and humidity sensor unit 232 may include a temperature sensor 232a and a humidity sensor 232b.

Depending on the embodiment, the sensor unit 230 may separately include a temperature sensor unit and a humidity sensor unit. The temperature sensor unit includes at least one temperature sensor, and the humidity sensor unit includes at least one humidity sensor.

Also, the oxygen ($O_2$) sensor 231a, the carbon monoxide (CO) sensor 231b, the hydrogen sulfide ($H_2S$) sensor 231c, the hydrogen ($H_2$) sensor 231d, the methane ($CH_4$) sensor 231e, and the temperature and humidity sensor unit 232 are arranged to correspond to the spaces 224a of FIG. 3 and configured to measure characteristics of air passing through the spaces 224a depending on a purpose thereof and provide measurement information to the control unit 210.

Since a portable gas measuring device requires a low power consumption design, it is preferable that sensors constituting the sensor unit 230 have characteristics of low power consumption and high sensitivity.

The configuration and function of the portable closed-space gas measuring device according to an embodiment of the present invention have been described above. A method of measuring gas using a portable closed-space gas measuring device according to an embodiment of the present invention will be described below.

Figure 5:
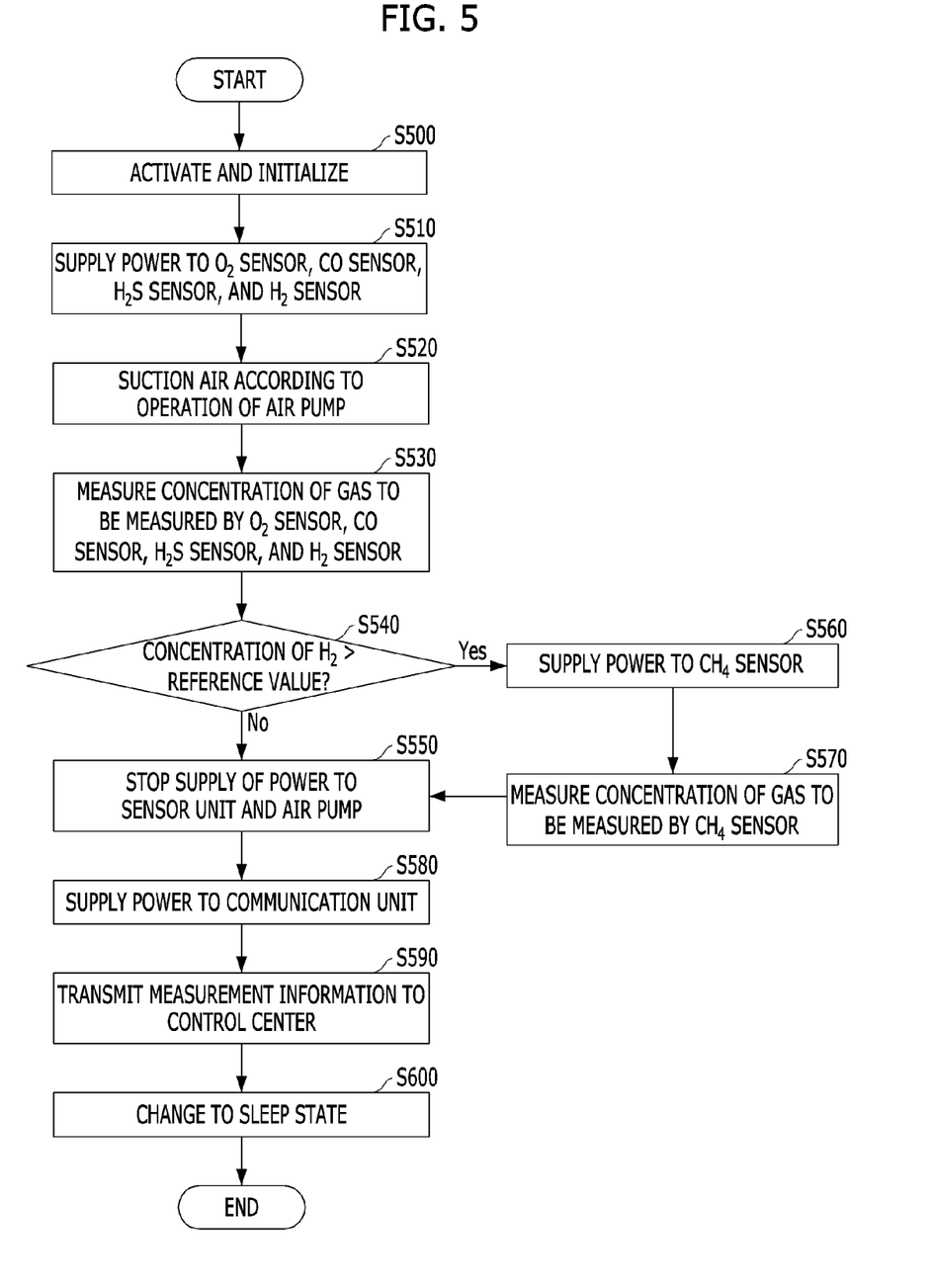
FIG. 5 is a flowchart showing of a method of measuring gas in a closed space according to an embodiment of the present invention.

FIG. 5 is a flowchart showing of a method of measuring gas in a closed space according to an embodiment of the present invention. The method may be applied to the portable closed-space gas measuring device shown in FIG. 2.

The method of measuring gas in a closed space will be described with reference to FIG. 5. The portable closed-space gas measuring device is assumed to be in the sleep state.

First, the gas measuring device 200 is initialized when the gas measuring device 200 is activated from the sleep state (S500), and power is supplied to the sensor unit 230 (S510).

In detail, an event signal for activating the gas measuring device 200 is input to the control unit 210. The event signal may be an interrupt generated by a timer included in the control unit 210, an operation start signal generated by the operation unit 270 according to a user's operation, or a wake-up signal input from the outside.

Like this, when the event signal is input to the control unit 210, the control unit 210 controls the power supply unit 250 to supply power to the sensor unit 230. In this case, the power supply unit 250 supplies power to the oxygen ($O_2$) sensor 231a, the carbon monoxide (CO) sensor 231b, the hydrogen sulfide ($H_2S$) sensor 231c, and the hydrogen ($H_2$) sensor 231d.

After a predetermined time for stable operation of the sensors passes, the control unit 210 operates an air pump of the air intake and exhaust unit 220 to suction air into the gas measuring device 200 (S520).

In this case, the control unit 210 controls the power supply unit 250 to supply power to the air pump.

Like this, when air is suctioned into the gas measuring device 200, the suctioned air moves along a movement path. The sensor unit 230 provided on the movement path of the air measures a concentration of gas to be measured that is included in the air (S530).

Measurement information that is measured in step S530 is provided to the control unit 210. The control unit 210 determines whether a concentration of hydrogen ($H_2$) exceeds a reference value (e.g., 0 ppm) (S540) and cuts off the power supplied to the sensor unit 230 and the air pump when the concentration thereof does not exceed the reference value (No in S540).

In this case, the control unit 210 controls the power supply unit 250 to cut off the power supplied to the sensor unit 230 and the air pump.

On the other hand, when it is determined that the concentration of hydrogen ($H_2$) exceeds the reference value (Yes in S540), the control unit 210 controls the power supply unit 250 to supply power to the methane ($CH_4$) sensor 231e (S560). When the power is applied thereto, the methane ($CH_4$) sensor 231e measures a concentration of methane ($CH_4$) gas included in the air after its operation is stabilized (S570).

In this case, measurement information measured in step S570 is provided to the control unit 210 and fed back to step S550, and the control unit 210 controls the power supply unit 250 to cut off the power supplied to the sensor unit 230 and the air pump.

After step S550, the control unit 210 controls the power supply unit 250 to supply power to the communication unit 240 (S580).

Subsequently, the communication unit 240 transmits the measurement information provided from the control unit 210 to a host system, for example, the control center 3 of FIG. 1 (S590). When a series of operations are complete, the gas measuring device 200 enters the sleep state (S600), and the operations of the gas measuring method according to an embodiment of the present invention are finished.

Since the closed-space gas measuring device according to an embodiment of the present invention is a portable device and uses an air intake pump and a special intake and exhaust structure, it is possible to precisely measure concentrations of oxygen and a harmful gas, and thus reduce a risk of suffocation or an explosion and also promote safety of a worker.

Also, since the closed-space measuring device according to an embodiment of the present invention can detect a high temperature using a temperature and humidity sensor, it is possible to detect a fire at an initial stage and thus minimize property damage.

Also, since the closed-space measuring device according to an embodiment of the present invention operates according to an algorithm for reducing energy consumption, it is possible to dramatically reduce battery consumption and thus use the device for a long time.

As a result, the closed-space measuring device according to an embodiment of the present invention is configured to measure gas in a closed space by applying new IoT technology, a technology for precisely measuring oxygen and a harmful gas, and a technology for designing for low power consumption. Thus, it is possible to provide a safe work environment to a worker in a closed space and prevent an accident.

It should be understood that although the present invention has been described above in detail with reference to the accompanying drawings and example embodiments, the description is illustrative only and various modifications may be made without departing from the spirit or scope of the invention. Thus, the scope of the present invention is to be determined by the following claims and their equivalents, and is not restricted or limited by the foregoing embodiments.

What is claimed is:

1. A portable gas measuring device for measuring gas in a closed space, the gas measuring device comprising:
   an air intake and exhaust unit configured to suction external air and discharge the suctioned air;
   a sensor unit configured to measure characteristics of the air suctioned by the air intake and exhaust unit;
   a communication unit configured to communicate with a host system;
   a power supply unit configured to supply power to the air intake and exhaust unit, the sensor unit, and the communication unit; and
   a control unit configured to control the air intake and exhaust unit, the sensor unit, the communication unit, and the power supply unit so that the sensor unit measures the characteristics of the air suctioned by the air intake and exhaust unit, and configured to transmit measurement information to the host system through the communication unit,
   wherein the control unit is activated from a sleep state by using a wake-up signal transmitted from the host system as an event signal and performs a predetermined operation after being activated.

2. The gas measuring device of claim 1, wherein the control unit is configured to be deactivated upon completion of performing the predetermined operation.

3. The gas measuring device of claim 1, wherein the communication unit includes at least one of a LoRa communication module, a Zigbee communication module, and a Bluetooth low energy (BLE) communication module.

4. The gas measuring device of claim 1, wherein the sensor unit includes an oxygen ($O_2$) sensor, a carbon monoxide (CO) sensor, a hydrogen sulfide ($H_2S$) sensor, a hydrogen ($H_2$) sensor, and a methane ($CH_4$) sensor.

5. The gas measuring device of claim 4, wherein the air intake and exhaust unit comprises:
   a body;
   an intake port formed at one side of the body and configured to suction external air;
   an exhaust port formed at another side of the body and configured to discharge the air suctioned through the intake port;
   an air pump configured to enable air to be suctioned through the intake port and discharged through the exhaust port; and
   a pipe configured to connect the intake port to the exhaust port,
   wherein the pipe includes spaces with a certain size in which the air stays for a predetermined time and a connector configured to connect the spaces.

6. The gas measuring device of claim 5, wherein the oxygen sensor, the carbon monoxide sensor, the hydrogen sulfide sensor, the hydrogen sensor, and the methane sensor are arranged to correspond to the spaces and configured to measure gas to be measured that is included in air passing through the spaces.

7. The gas measuring device of claim 4, wherein the control unit controls the power supply unit to supply power to the oxygen sensor, the carbon monoxide sensor, the hydrogen sulfide sensor, and the hydrogen sensor, and controls the power supply unit to supply power to the methane sensor when a concentration of hydrogen measured by the hydrogen sensor exceeds a reference value.

8. The gas measuring device of claim 1, wherein the control unit is configured to control the air intake and exhaust unit, the sensor unit, the communication unit, and the power supply unit after the control unit is activated from the sleep state according to the event signal.

9. The gas measuring device of claim 8, wherein the control unit is activated by using an interrupt generated by a timer included in the control unit as the event signal.

10. The gas measuring device of claim 9, wherein the timer included in the control unit generates the interrupt at a predetermined time.

11. The gas measuring device of claim 10, wherein the predetermined time is received as set by the host system or directly set by a user.

12. The gas measuring device of claim 8, further comprising an operation unit configured to generate a plurality of electric signals according to an operation of a user to control the gas measuring device,
   wherein the control unit is activated by using an operation start signal generated by the operation unit as the event signal.

13. The gas measuring device of claim 12, wherein the operation unit includes a plurality of switches for generating different electric signals.

14. The gas measuring device of claim 13, wherein the operation unit includes a start button for generating an operation start signal and an end button for generating an operation end signal.

15. The gas measuring device of claim 1, wherein the control unit controls the power supply unit to supply power to the sensor unit, supply power to the air intake and exhaust unit after a stabilization time, and stop the supply of power to the sensor unit and the air intake and exhaust unit when the measurement of the sensor unit is complete, and then supply power to the communication unit.

16. The gas measuring device of claim 1, further comprising:
   a warning unit configured to warn about a danger according to control of the control unit;
   an external power connector connected to the power supply unit and configured to supply external power to the power supply unit; and
   a display unit configured to display a state of the gas measuring device according to control of the control unit.

17. The gas measuring device of claim 16, wherein the display unit comprises:
   a first display composed of a plurality of light emitting diodes (LEDs) and configured to use light to display the state of the gas measuring device; and
   a second display configured to use figures or characters to display the state of the gas measuring device.

18. The gas measuring device of claim 17, wherein the second display displays a screen for setting a threshold of information measured by the sensor unit and an interval at which the measurement information is transmitted and provides information input through the screen to the control unit.

19. A low-power gas measuring method using a portable gas measuring device for measuring gas in a closed space, the portable gas measuring device including an air intake and exhaust unit, a sensor unit, a communication unit, and a power supply unit, the low-power gas measuring method comprising:

receiving, by the portable gas measuring device in a sleep state, a wake-up signal transmitted from a host system;

activating the portable gas measuring device by the wake-up signal as an event signal;

controlling the air intake and exhaust unit, the sensor unit, the communication unit, and the power supply unit according to the activation; and measuring characteristics of air suctioned by the air intake and exhaust unit, and transmitting measurement information to the host system through the communication unit.

20. The low-power gas measuring method of claim 19, wherein the activating includes activating by using an interrupt generated by a timer as the event signal.

21. The low-power gas measuring method of claim 20, wherein the timer generates the interrupt at a predetermined time.

22. The low-power gas measuring method of claim 21, wherein the predetermined time is received as set by the host system or directly set by a user.

23. The low-power gas measuring method of claim 19, wherein the portable gas measuring device further comprises an operation unit configured to generate a plurality of electric signals according to an operation of a user to control the portable gas measuring device, and wherein the activating includes activating by using an operation start signal generated by the operation unit as the event signal.

24. The low-power gas measuring method of claim 23, wherein the operation unit includes a plurality of switches for generating different electric signals.

25. The low-power gas measuring method of claim 24, wherein the operation unit includes a start button for generating an operation start signal and an end button for generating an operation end signal.

* * * * *